(12) United States Patent
Koivumaa et al.

(10) Patent No.: US 7,797,039 B2
(45) Date of Patent: Sep. 14, 2010

(54) METHOD FOR RECOGNIZING THE HEARTBEAT AND FOR CALCULATING QUANTITIES ACQUIRED FROM THE HEARTBEAT

(75) Inventors: Veikko Koivumaa, Espoo (FI); Mikko Martikka, Vantaa (FI); Juha Kylliäinen, Siilinjärvi (FI); Eero Punkka, Helsinki (FI); Arto Remes, Kuopio (FI); Pekka Tolvanen, Kuopio (FI)

(73) Assignees: Mega Elektroniikka Oy, Kuopio (FI); Suunto Oy, Vantaa (FI)

( * ) Notice: Subject to any disclaimer, the term of this patent is extended or adjusted under 35 U.S.C. 154(b) by 54 days.

(21) Appl. No.: 11/393,332

(22) Filed: Mar. 29, 2006

(65) Prior Publication Data

US 2006/0173370 A1    Aug. 3, 2006

Related U.S. Application Data

(63) Continuation of application No. PCT/FI2004/000565, filed on Sep. 28, 2004.

(30) Foreign Application Priority Data

Oct. 3, 2003    (FI)    ................................. 20031436

(51) Int. Cl.
*A61B 5/0456*    (2006.01)
(52) U.S. Cl. ..................... 600/521; 600/509; 600/520; 600/546; 600/382; 600/384; 600/388; 600/393; 128/901
(58) Field of Classification Search ................. 600/382, 600/384, 388–390, 393, 509, 519
See application file for complete search history.

(56) References Cited

U.S. PATENT DOCUMENTS 4,459,993 A * 7/1984 Foreman ..................... 600/519
4,681,118 A * 7/1987 Asai et al. .................. 600/387

(Continued)

FOREIGN PATENT DOCUMENTS

JP    10-26239    10/1998

(Continued)

OTHER PUBLICATIONS

Machine Translation of Yasuto (JP publication No. 10262939), obtained May 7, 2009.*

(Continued)

*Primary Examiner*—Kennedy J Schaetzle
(74) *Attorney, Agent, or Firm*—Harrington & Smith

(57) ABSTRACT

The present invention relates to a method for recognizing and measuring heartbeat in physical training, in which method individual heartbeats are recognized and measured from the electrical signal of the heart, the EKG signal, on the area of waist and/or on the body area below the waist by means of two or more electrodes (2, 3) integrated to an outfit (1) or to a part of an outfit, and/or by means of two or more electrodes integrated to one or several wearable sensors, and for calculating various quantities describing the function of the heart. In the method in accordance with the invention, for recognizing and measuring heartbeat, the signals received from the heart are processed and examined with two or more different ways for improving the reliability of calculation and for decreasing the impact of noises.

8 Claims, 7 Drawing Sheets

U.S. PATENT DOCUMENTS

Figure 1:
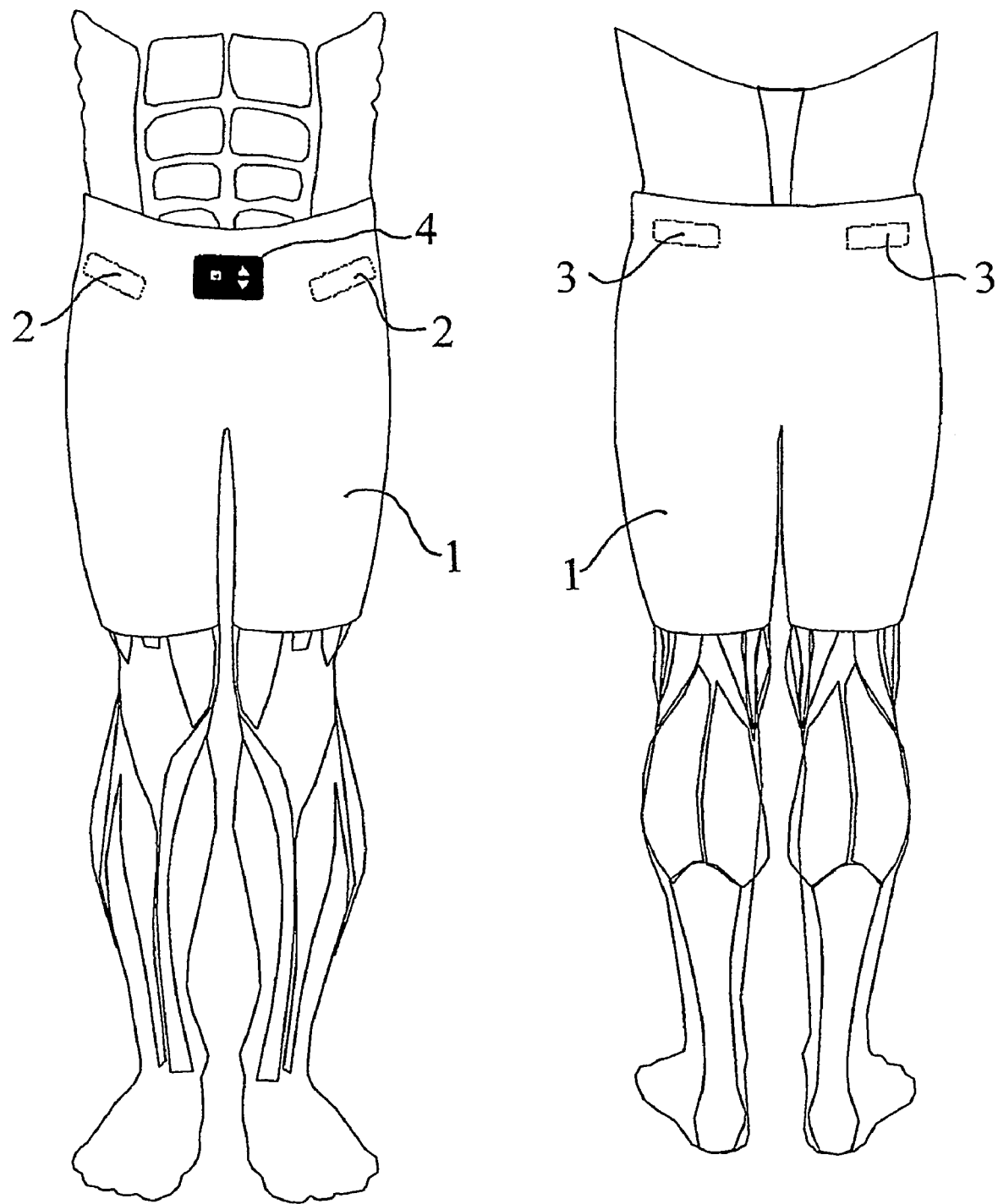

| | | | |
|---|---|---|---|
| 4,729,377 A * | 3/1988 | Granek et al. | 600/393 |
| 4,763,660 A | 8/1988 | Kroll et al. | 128/640 |
| 4,773,427 A * | 9/1988 | Inoue et al. | 600/509 |
| 5,353,793 A * | 10/1994 | Bornn | 600/386 |
| 5,474,083 A | 12/1995 | Church et al. | 128/733 |
| 5,876,350 A * | 3/1999 | Lo et al. | 600/519 |
| 5,908,393 A | 6/1999 | Albrecht et al. | 600/509 |
| 6,553,251 B1 * | 4/2003 | Lahdesmaki | 600/519 |
| 6,571,115 B2 * | 5/2003 | Axelgaard et al. | 600/388 |
| 6,584,344 B2 * | 6/2003 | Hannula | 600/509 |
| 6,728,577 B2 * | 4/2004 | Minogue et al. | 607/48 |
| 2002/0045836 A1 * | 4/2002 | Alkawwas | 600/509 |
| 2003/0065269 A1 * | 4/2003 | Vetter et al. | 600/503 |

FOREIGN PATENT DOCUMENTS

| | | |
|---|---|---|
| WO | WO 96/14796 | 5/1996 |
| WO | WO 02/071935 A1 | 9/2002 |
| WO | WO 03/082103 A1 | 10/2003 |
| WO | WO 2004/052190 A1 | 6/2004 |

OTHER PUBLICATIONS

Bensadoun, Y., et al., "Multidimensional Adaptive Method for Cancelling EMG Signal from the ECG Signal", 1995, IEEE-EMBC and CMBEC, Theme 1: Cardiovascular System, pp. 173-174.

* cited by examiner a)

b)

c)

a)

b)

c)

METHOD FOR RECOGNIZING THE HEARTBEAT AND FOR CALCULATING QUANTITIES ACQUIRED FROM THE HEARTBEAT

CROSS REFERENCE TO RELATED APPLICATION

The application is a continuation of International Patent Application No. PCT/FI2004/00565 filed Sep. 28, 2004.

The present invention relates to a method for recognizing and measuring heartbeat in physical training, in which method individual heartbeats are recognized and measured from the electrical signal of the heart, the EKG signal, on the area of waist and/or on the body area below the waist by means of two or more electrodes integrated to an outfit or to a part of an outfit and/or by means of two or more electrodes integrated to one or several wearable sensors and for calculating various quantities describing the function of the heart.

BACKGROUND OF THE INVENTION

It is generally known that from the electrical signal of the heart, the so-called EKG signal, individual heartbeats may be recognized and that various quantities describing the function of the heart may be measured from those. Usually, the EKG signal is measured by means of electrodes placed in various parts of the body on the skin surface. Quantities describing heart functions are, among others:

the number of heartbeats/minute that is the pulse the difference in time between two heartbeats and its variations, that is the pulse interval the total number of heartbeats during a certain performance/time period that is the number of pulses In addition, quantities that may be monitored and controlled may be measured from the shape, amplitude and the variation differing from the normal rhythm (arrhythmia)

So-called pulse monitors, which are in use today, are based on recognizing heartbeats by means of a separate sensor placed on the chest, as the strongest EKG signal may be detected on the chest. Typically, a sensor is a solid, elastic band by shape, the tightness of which is regulated with an elastic ribbon. Electrodes in the band are generally made of electro-conducting plastic. Especially during long-term performances, and while sweating a lot, the band slips away from its place or it may feel uncomfortable or cause abrasions. The measuring of pulse is generally based on recognizing the QRS peak being a part of the EKG signal. In a pulse band the measuring is carried out between two electrodes (the unipolar measuring), which is not an absolutely reliable method for recognizing heartbeats, while various movement disturbances may cause to the signal almost identical pulses compared to a heartbeat or parts of it. Bipolar measuring is used in clinical EKG measuring, that is measuring is done with three electrodes, in which case both positive and negative components are included in the signal. Therefore, in the EKG signal, in addition to the QRS peak, also other essential shapes of the heartbeat are visible, such as the so-called P-wave and the ST-segment. While using three electrodes, the EKG signal may be measured by means of various, so-called Beethoven connections, either separately or simultaneously. In various connections different characteristics of the heartbeat are emphasized, what makes it easier to examine the function of the heart including the recognition of individual heartbeats.

Measuring pulse during sports in water, such as swimming, is especially inconvenient by means of a pulse band. While moving in water, water has access between the skin and the pulse band, and the impurities in water (salt, chlorine and etc., among others) cause a short circuit between the electrodes of the pulse band, in which case the measuring signal is disturbed. In addition, the resistance of water flow tends to move the pulse band on the chest along the body downwards, due to which the pulse band is inconvenient to use. The measuring of the pulse of swimmers with present methods is carried out by interrupting the swimming at the ends of the pool where the swimmer or an assistant uses a separate hand-held band for measuring. Therefore, the interruption of the performance does not give correct information about the pulse rate of the swimmer and is impractical.

Electrodes used in clinical measurements are attached with adhesive or with a suction cup onto the skin, and the quality of the signal is secured with a special gel or similar improving conductivity. In use outside clinical environment, for example during a physical exercise, these kinds of electrodes have proved to be impractical despite of their reliability.

The object of the invention is to provide a method for recognizing and measuring of heartbeat, in which method disadvantages connected with present methods are eliminated. Especially, the object of the invention is to provide a method in the use of which reliable measuring results may be gathered not only from the chest area but also from elsewhere. Furthermore, the object of the invention is to provide a method, in the use of which the measuring electrodes stay in place and in reliable contact also during a long-term measurement and during various movement disturbances. The object of the invention is also to provide a user with options which are easier to use and more advantageous for measuring the pulse.

DESCRIPTION OF THE INVENTION

In the method in accordance with the invention, the signals received from the heart are processed and examined with two or more different ways for improving the reliability of calculation and for decreasing the impact of noises.

There are various kinds of options for processing and examining signals from the heart in two or more different ways. In one application, the heartbeats are measured from the same electrodes and with the same connection, but the signals are conducted simultaneously to two different channels. The low frequency noise is filtered from one channel and the high frequency noise from the other channel respectively. After this, the signals are summed together, in which case the characteristics of the heartbeat amplify each other and are better identified from the signal level of the noise. It is easier to identify individual beats from the combined signal and therefore calculations of quantities from those are more reliable. While filtering and combining signals, also other recognized, as such, filter combinations and processing methods of signals and calculations methods of quantities may be used.

In the method in accordance with the invention, heartbeats are recognized from one or several EKG signals measured from at least two electrodes placed on an outfit, such as on trunks or some other outfit reaching the waist or below it, by means of signal processing electronics and programme placed in a measuring module. A separate sensor on the chest is not needed. Thanks to an outfit of the right size, for example trunks made of elastic cloth, electrodes stay in the right place during the whole time of performance maintaining a reliable contact between the electrodes and the skin. For recognizing heartbeat also a separate wearable sensor may be used, to which the needed electrodes are integrated. This kind of sensor may be placed to the measuring point either by attaching the sensor to an outfit covering the spot in question or it may be worn by means of rubber band, belt or some other suitable aid like present bands used for measuring heartbeats.

In the next advantageous application of the invention, heartbeats are examined with two or more signals received from different parts of the body for improving the reliability of calculation and for decreasing the influence of noises. In this way at least two signals which are simultaneous but differ somewhat from each other may be received from the heart. However, as the heartbeat in both signals appears in practise at the same time, recognizing of beats from among possible noise is easier and more reliable. After this, recognized, as such, processing methods of signals and calculation methods of quantities may be applied to both signals.

In the next advantageous additional application of the invention two or more signals from heartbeats are processed in ways differing from each other, for example, by using various filtering, for improving the reliability of calculation and decreasing the influence of noise. These signals are processed and examined in two or more simultaneous or parallel or parallel and successive different ways. By means of this kind of method, it is possible to identify momentary and/or repeated movement noise and/or EMG noise caused by body muscles seen on one channel and to ignore them in calculations and analyses based on recognizing heartbeat.

In one additional application of the method in accordance with the invention signals gathered for measuring from a moving person are processed for decreasing the influence due to muscle and/or movement noise by means information received from EMG and/or movement signals measured simultaneously. In this way, signals of sufficiently good quality may be gathered also while measuring the EKG from the waist and area below it, where the EKG signal is lower by amplitude and more sensitive to noise than in measurements carried out on the chest.

In an application of the method in accordance with the invention two electrodes are used, which have been placed on the pelvis area and on the lower dorsum area and the EKG signal is measured unipolar. This method of measuring is suitable when the amount of movement noise in signal is not significant. For recognizing heartbeat also simple peak recognition is enough. A measuring device realized in this way is simple to manufacture and, therefore, economical by cost.

In the next advantageous additional application of the invention, heartbeat is measured with three electrodes, which have been placed on the pelvis and the lower dorsum area. The EKG signal may be measured bipolar, in which case recognition of heartbeats from the signal is easier than in unipolar measurement.

In the next advantageous additional application of the invention, heartbeat is measured with at least four electrodes, which have been placed on the pelvis and the lower dorsum area. In this case the EKG signal may be measured bipolar and, in addition, several connections options may be chosen for finding, among others, a signal which has as big as possible amplitude or which includes less movement noise or EMG noise.

In the next advantageous additional application of the invention the EKG signal of the heart is measured with two channels bipolar by using three electrodes/channel such that both channels examine the heart and its electric functioning from different directions. From a bipolar EKG signal, it is possible to detect the heartbeat by recognizing in addition to QRS peaks also the other earlier described shapes of the normal EKG curve. From one channel QRS peaks are recognized by a simple pulse detection method and from the other channel other shapes by image detection algorithms. In that case, the recognition of individual heartbeats is more reliable also in cases when the signal includes movement noise.

In the next advantageous additional application of the invention, at the same time with the EKG signal, also EMG signals indicating the activity of foot muscles are measured as well as movement signals of the body and extremities by means of acceleration or some other motion sensors placed on the body. In that case noise caused by movements and muscle activities is filtered from the EKG signal by combining the signals from noise sources, for example, as opposite in phase or by some other way suitable for the purpose.

In an advantageous application of the invention, the pulse is measured during physical exercise in water, in which case the electrodes needed in the measurement are place on the outfit worn in water, such as a swimming suit. In swimming trunks, the place for electrodes is on the area of the waist of the trunks. In other swimming suits, electrodes may be placed also such that they are near the chest. In that case, the strength of the EKG signal is better and the measurement is less exposed to various movements' noises, in which case also the number of needed measuring electrodes may be decreased. In an advantageous additional application, the surroundings of the electrodes and the suit cloth on the electrodes are made denser and/or impregnated with a waterproof substance or film. These, on one hand prevent the access of water between the electrodes and the skin, and on the other hand isolate the electrodes from one another.

In an advantageous additional application of the invention a waterproof module is attached to a swimming suit, in which module there are, in addition to an EKG amplifier, electronics and programme for calculating the parameters of the pulse as well as a memory unit for saving the results, and the functioning of which module is controlled by an external device.

Instead of a present wrist computer-pulse rate module-type method, the measuring of pulse during swimming or other physical exercise in water is carried out advantageously by using a waterproof module attached to the swimming suit or similar, in which module there are, in addition to an EKG amplifier, the electronics and programme for calculating the pulse as well as a memory unit for saving the results. The functioning of it may be controlled with an external device. The measuring is started, for example, by means of a wrist computer before entering water and respectively stopped after physical exercise, such as swimming, in which case there is no need to carry the wrist computer while swimming. After swimming, the pulse data in the module will be transmitted, for example, wirelessly to a wrist computer or to a PC for examination.

DESCRIPTION OF THE INVENTION

Figure 2:
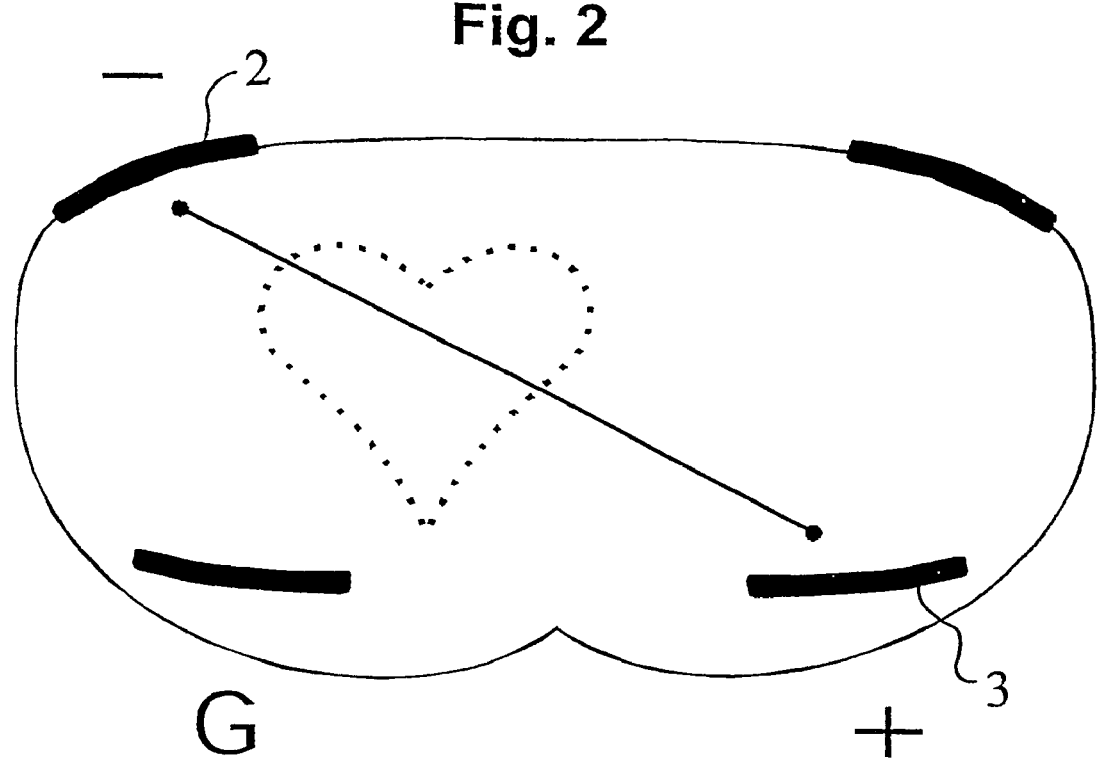
Figure 3:
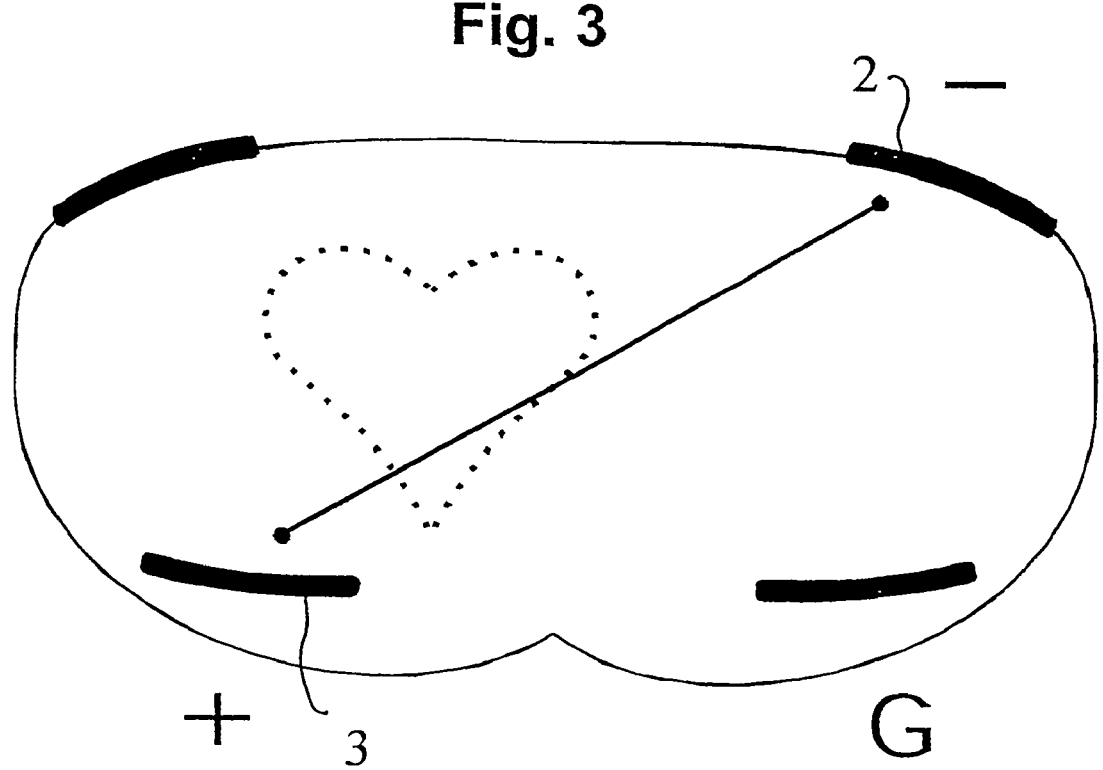
Figure 4:
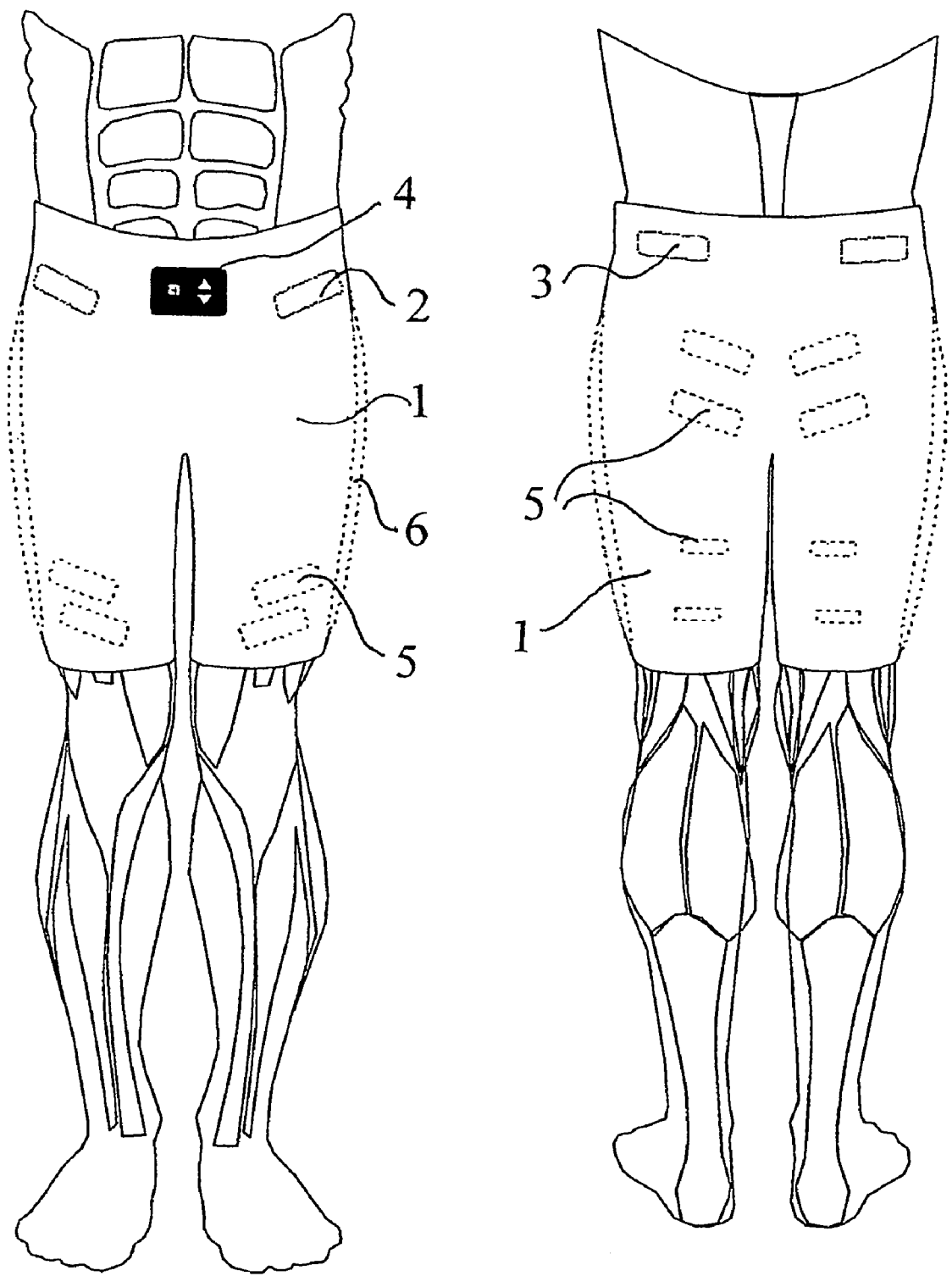
Figure 5:
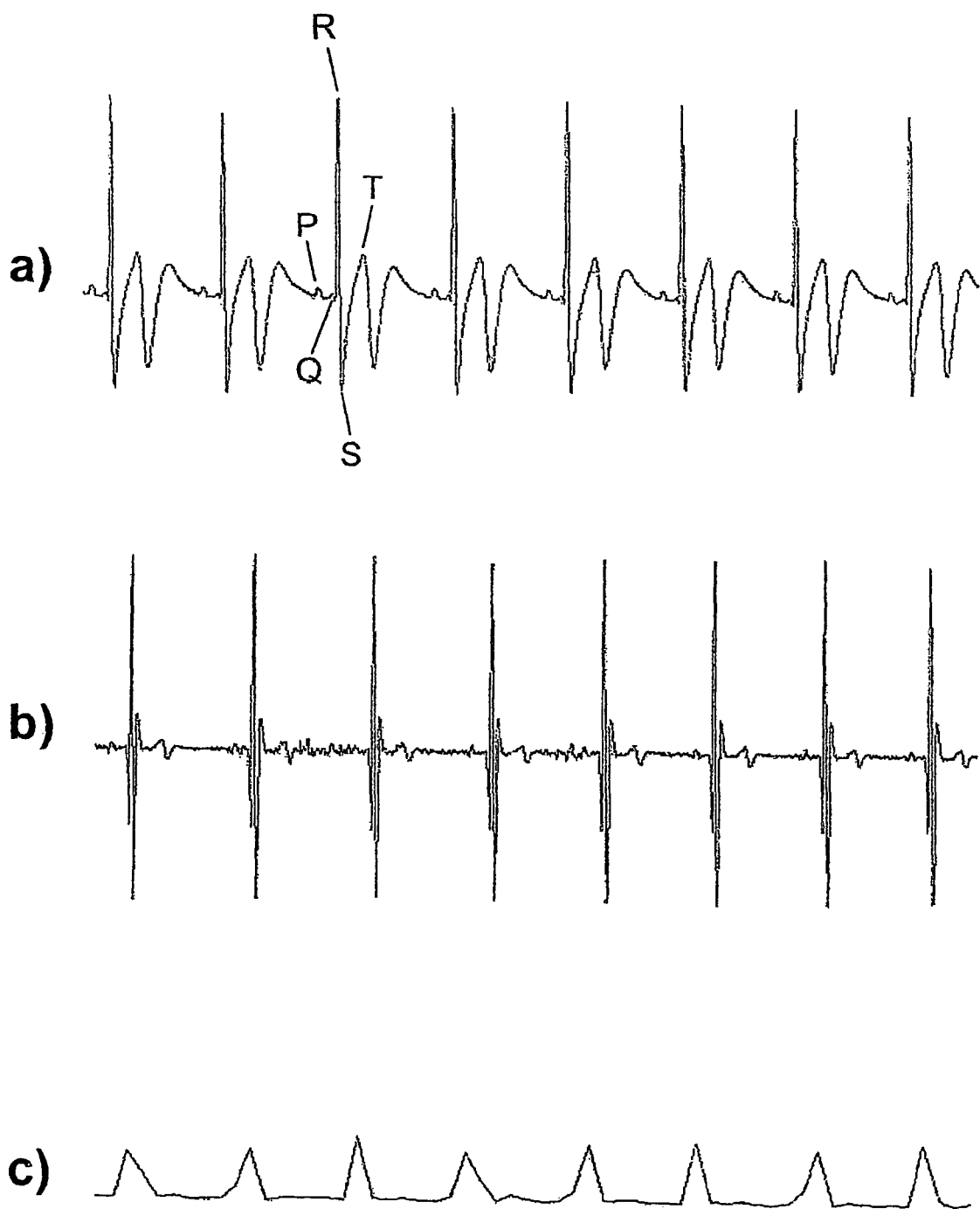
Figure 6:
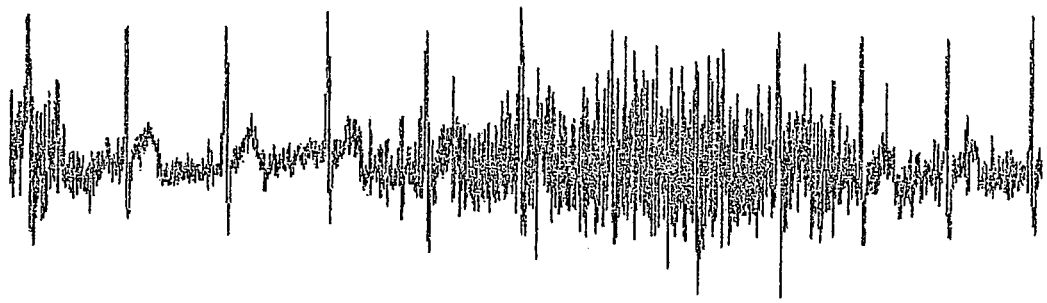
Figure 6:
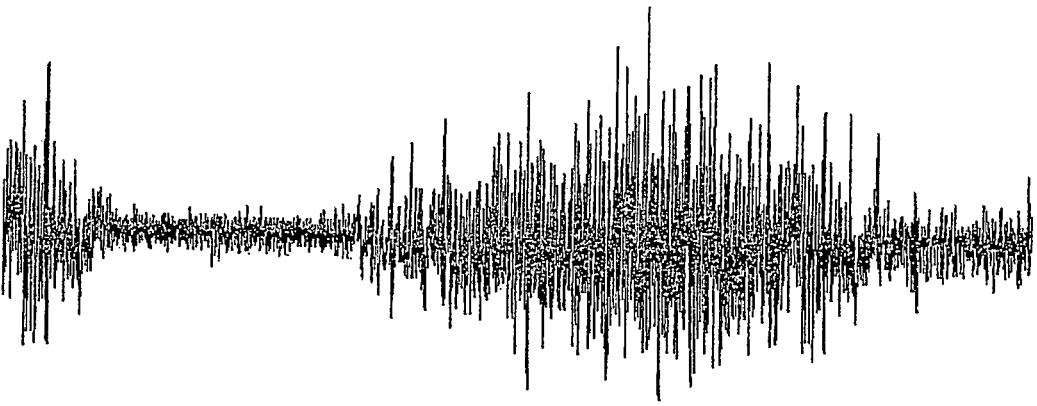
Figure 6:
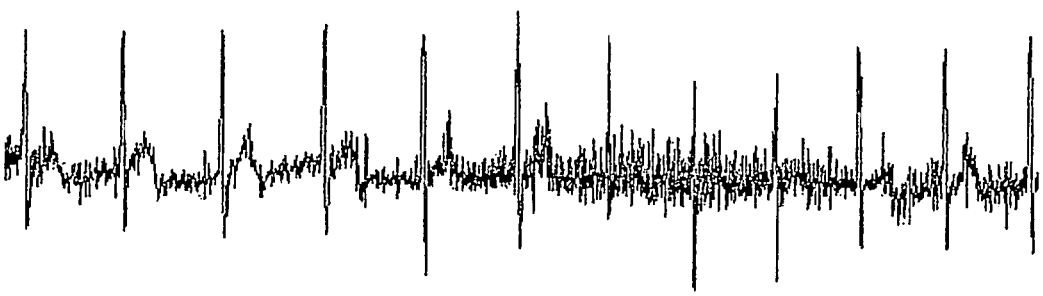
Figure 7:
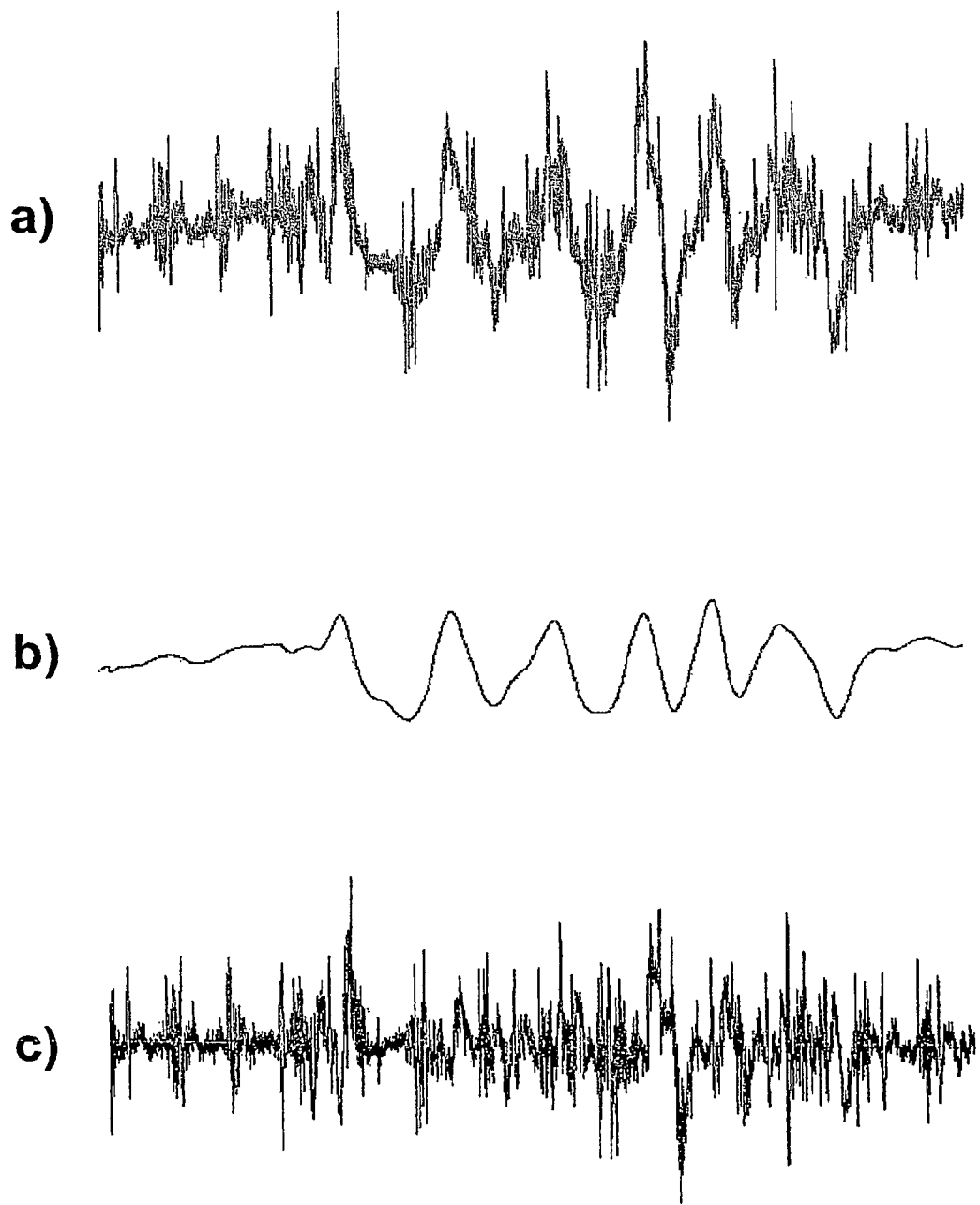
Figure 8:
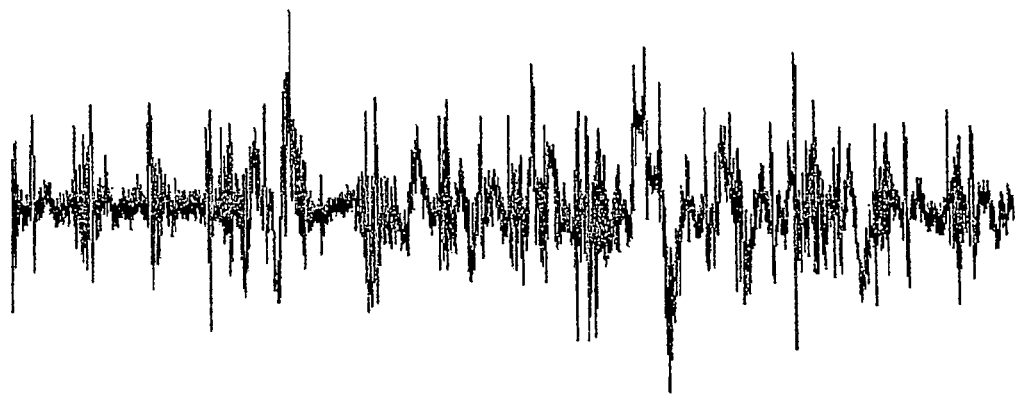
Figure 8:
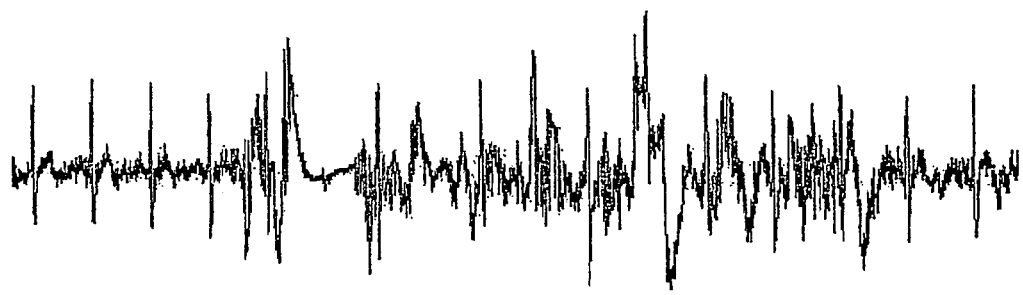
Figure 8:
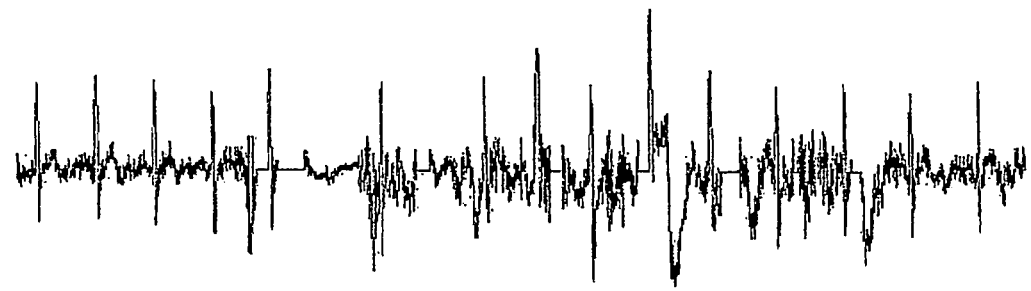

Next, the invention will be explained in more detail with reference to the accompanying drawings, in which, FIG. 1 illustrates an outfit and a device for applying the method in accordance with the invention, FIGS. 2 and 3 illustrate the placing of the electrodes on the waist and two different connection options viewed from above, FIG. 4 illustrates another outfit in accordance with the invention for applying the method, FIG. 5 illustrates examples of different filtering of the signals and further processing of the signals, FIG. 6 illustrates the filtering of EMG noise from the EKG signal, FIG. 7 demonstrates the way movement noises are filtered from the EKG signal, FIG. 8 illustrates the filtering of EMG noise from the EKG signal and eliminating false pulses.

FIG. 1 illustrates an outfit, trunks, with electrodes placed on desired places. Recognised textile electrodes suitable for the purpose are used as electrodes but also other kind of electrodes may be used in other applications. These electrodes have been connected to a device for monitoring and measuring attached to the trunks and shown in the figure. The signals from the electrodes are connected to the device by means of conducting fibres attached to the trunks or by means of some other recognized conductor. The electrodes, conductors and connections on outfits are washable and durable.

The device for monitoring and measuring may be placed on the same outfit, it may be situated on a different outfit or in some device, which the user carries. The device may be placed in a medium which the user uses for moving, and/or the desired information may be transmitted wirelessly in a recognized way, as such, to one or several devices placed at a distance.

In an application in accordance with the figures the electrodes have been placed in accordance with the method on the lower dorsum and pelvis area on such places that, on the one hand, EMG signals created by muscles on that are as small as possible and, on the other hand, on places where the other tissues under the skin are as thin as possible and do not unnecessary damp the EKG signal coming from the heart. A placement like this has been illustrated in FIGS. 2 and 3, in which the electrodes (4 electrodes) are placed on those places on the body, where the innominate bones are at the closest to the skin surface. Two measuring channels have been connected to these electrodes such that they partly make use of the same electrodes. The connections of the channels and the directions of the bipolar measurement are also illustrated in FIGS. 2 and 3. In FIG. 2 the signal is measured between "+" and "−" electrodes by using the electrode G as a reference electrode. In FIG. 3 there is a similar but reverse connection. In figures the electrodes placed below are present in both connections but their purpose of use differs from each other in different connections. On one channel the EKG signal is measured emphasizing the left side of the body, and on the other channel emphasizing the right side, respectively, in which case the electric function of the heart is seen differently on both channels. With making use of this kind of sorting, it is possible to make the recognizing of heartbeat as reliable as possible during exercise with alternating rhythm of feet, for example, during walking, running or cycling, as in the different phases of rhythm at least on one side of the body, there is a EKG signal sufficiently without noise in terms of recognizing.

On the channels also filtering of signals differing from each other may be used, in which case it is possible to remove errors caused by external noises from the signals. For example, on one channel noises of high frequency caused by shakes of the body are dampened, in which case also so-called QRS peak of the EKG signal is dampened but the other shapes of the heartbeat remain recognizable. On the other channel, respectively, noises of low frequency caused by movements of extremities may be dampened, in which case the QRS peak not being dampened is distinguished easier from the signal, but, on the other hand, the other characteristics of the heartbeat are dampened. In addition, on different channels different composite and band pass filters or methods adapting the signal may be used, such as rectifying, cutting off the negative or the positive side etc.

FIG. 4 illustrates otherwise the same device and the trunks as in FIG. 1, but they have measuring electrodes for measuring the EMG signal from femoral and gluteal muscles and uniform reference electrodes on the sides of thighs. In addition, there is an acceleration sensor of one, two or three direction integrated to the device for recognizing movements of the body. EMG signals and the signals coming from the acceleration sensor are processed in the same monitoring and measuring device, which measures the EKG signals.

In the method in accordance with the invention simultaneous EMG and acceleration signals are facilitated for filtering noise from the EKG signal. In the EKG signal measured in accordance with the method there may be EMG signal seen through the electrodes measuring the EKG, which EMG signal is created in the muscles near the electrodes. When the source of these EMG noises is known, it may be filtered from the EKG signal. For example, the EMG signal caused by the left foot is connected to the EKG electrodes placed on the left side of the pelvis. When the muscle activity of the left foot is measured simultaneously with electrodes on the femur and/or glutei, the EMG signal from those may be fed as opposite in phase in accordance with the EKG signal, in which case the share of the EMG signal is dampened, and the characteristics describing the heartbeat become more clearly visible. While the EMG signal in foot muscles seen through the EKG electrodes is somewhat damper compared to the signals from the muscles of femur and glutei, the signal taken straight from femur and/or glutei used for filtering may be dampened suitably before being fed according to the EKG signal. As a filtering signal for the EKG, also the EMG signals from the foot on the other side may, respectively, be used more dampened if necessary.

In addition, noises caused by movements may be filtered from the EKG signal by facilitating signals from acceleration or some other motion sensors placed on the body surface. Filtering methods are in principle the same as the methods described earlier by means of the EMG signals. Typical noises to be filtered are shakes transmitted through feet while running to an electrode and leads, which shakes are connected to the EKG signal through muscles and bones.

In FIGS. 5 and 6 some typical filtering and processing principles of the EKG signal in accordance with the invention are presented:

In FIG. 5*a*) there is a normal unfiltered EKG signal, which has been measured on a test person in rest. In the signal all typical shapes and characteristics (P, Q, R, S, T) are seen and there is not any noise in the signal. A heartbeat may be recognized either by pulse detection from QRS peak or by image detection from the wholeness of, for example, the QRS-peak and the ST-segment. In case the person measured is moving, there will be movement noise connected to the signal in which case the recognition of beats will be significantly more difficult.

FIG. 5*b*) illustrates an EKG signal, from which a part of the low frequencies has been filtered. Compared to a normal EKG signal, the QRS peaks are of the same volume by amplitude, but the other shapes typical to a heartbeat have dampened. This kind of filtering prevents the connection of fading of the low frequency basic level to the signal, in which case the recognition of beats is still possible.

The signal in FIG. 5*c*) has been formed by rectifying first the bipolar EKG signal and after that the signal has been strongly filtered with a steep band pass filter. A pulse line occurs as an end result, in which pulse line heartbeats have dampened significantly by amplitude, but the pulses are clear and easy to be counted. With this method, it is possible to have a useful signal from a very noisy measuring situation.

In FIG. 6*a*) there is an example of an EKG signal measured with a connection in accordance with FIG. 2, in which the EMG signal, caused by the left gluteal muscle, is seen. When muscles have been strongly activated, for example, during turning a bicycle shaft, the EKG signal gets such noise that the recognition of heartbeat from the signal is difficult.

In FIG. 6b) the EMG signal of gluteal muscles, recorded simultaneously with the signal in FIG. 6a) measured with electrodes in FIG. 4, is illustrated. While comparing these signals with each other it may be seen that the noise in the EKG signal is like the EMG signal by shape although of different size by amplitude.

In FIG. 6c) there is an example of a filtering carried out by means of the EMG signal. Combining an EMG signal in accordance with FIG. 6b) inverted and/or dampened in a suitable way to the EKG signal in accordance with FIG. 6a), the end result is a new signal, in which heartbeats are distinguished more clearly than in the original EKG signal, and they can also be recognized programmatically.

The EKG signal in FIG. 7a) is an example of a signal which includes low and high frequency movement noises as well as EMG noise like in FIG. 6b). This kind of signal occurs typically while running when the EKG signal is measured with the connection in FIG. 2.

FIG. 7b) illustrates a vertical acceleration signal measured from a motion sensor placed on the body, which signal has been filtered and averaged such that there are mainly the low frequency motions left in the signal. While comparing this signal with the EKG signal in FIG. 7a), it is seen that the basic level fading of the EKG signal reminds the motion signal in FIG. 7b).

FIG. 7c) illustrates a new combined signal, in which from the original EKG signal in FIG. 7a) the basic level fading has been removed in a suitable way by means of inverted and dampened motion signal in accordance with FIG. 7b). In the remaining signal, the heartbeats are better visible than in the original, but there is still high frequency noise components left.

FIG. 8a) presents both the filtered EKG signal in accordance with FIG. 7c) and the EMG signal from foot muscles measured simultaneously with the EKG signal. By examining the two signals, it may be noticed that the pulse frequency of the heart and the stepping rhythm seen in the EMG signal differ from each other and, in addition, that the regular noise in the EKG signal originate partly from muscle activity. When the muscle noise is removed, by means of a suitably attenuated EMG signal in FIG. 8a), from the signal in FIG. 7c, the result will be a EKG signal in accordance with FIG. 8b), in which pulses recognized as heartbeats can be detected as well as some noise pulses.

In calculating actual results, such as the pulse or the pulse interval, for example, in addition to the earlier described filtering methods also filterings based on recognizing the QRS peak are used. These kinds of methods represent, for example, analyses of the width of pulse or of exceeding threshold value, and rejection algorithm of false pulses. For example, the difference in time of two heartbeats, that is, QRS peaks may be, at the shortest, about 0, 25 sec. corresponding to the pulse rate 240 beats per minute. Based on this, from the two peaks too close to each other, one may be rejected as noise. When from the signal in FIG. 8b) pulses indicated false are removed, the pulse line in accordance with FIG. 8c) will remain, from which the average pulse and the pulse interval can be calculated by using various averaging methods.

By using filtering and processing methods described earlier, either together or separately, and by using other recognized methods, heartbeats can be recognized reliably also from an EKG signal with noise. Reliability may also be improved by measuring the EKG with two or more channels simultaneously by using different connections in different channels and by measuring from different parts of the body.

The invention is not limited to the presented advantageous applications, but it can vary within the frames of the idea of the invention formed in the claims.

The invention claimed is:

1. Method for recognizing and measuring heartbeat during physical training, comprising:
   recognizing individual heartbeats from ECG signals of a heart from an area of a waist and/or on an area of a body below the waist by means of electrodes integrated into an outfit or to a part of an outfit and/or by means of electrodes integrated to one or several wearable sensors, which electrodes are placed on different parts of the body
   measuring two or more of the ECG signals received from the heart simultaneously from different directions from the heart by means of three or more of said electrodes for recognizing the individual heartbeats and measuring a time difference between the individual heartbeats, comprising receiving at least two of the ECG signals of one of the heartbeats which are simultaneous but differ from each other,
   processing and analyzing the ECG at least two different ways to highlight moments of QRS peaks of the heartbeats for improving reliability of calculation and for decreasing impact of disturbances,
   processing the ECG signals, taken from a moving person for analysis, by means of information from simultaneously measured EMG signals of this moving person decreasing influence of muscle noises.

2. Method in accordance with claim 1, comprising
   measuring the heartbeats with at least four of the electrodes, which have been placed on a pelvis and a lower dorsum area.

3. Method in accordance with claim 1, comprising:
   measuring EMG signals indicating the activity of leg muscles, at a same time as the ECG signals, as well as movement signals of the body and its extremities by means of acceleration or other motion sensors attached on the body, and
   filtering movement noises away from the ECG signals by combining EMG signals or signals from motion and acceleration sensors.

4. Method in accordance with claim 1, comprising:
   measuring the heartbeats during physical exercise in water, wherein the electrodes measuring the heartbeats are placed on the outfit used in the water.

5. Method in accordance with claim 4, comprising:
   providing surroundings of the electrodes and a cloth on the electrodes that are dense and/or impregnated with a waterproof substance or film, which prevents access of water between the electrodes and the skin, and isolates the electrodes from one another.

6. Method in accordance with claim 4, comprising:
   attaching a waterproof module to the outfit used in the water, wherein the module comprises an ECG amplifier, electronics and programming needed for calculating parameters of the heartbeat as well as a memory configured for saving results.

7. A method comprising:
   recognizing and measuring individual heartbeats from ECG signals of a heart from an area of a waist and/or on a body area below the waist by electrodes integrated into an outfit and/or integrated into part of an outfit and/or on at least one wearable sensor;

determining a time difference between the individual heartbeats from at least two of the ECG signals measured simultaneously from different directions from the heart by means of at least three of the electrodes; and analyzing the at least two ECG signals in at least two different ways to highlight moments of QRS peaks of the heartbeats to thereby improve reliability of the analyzing of the ECG signals for decreasing impact of disturbances, processing the BCG signals, taken from a moving person for analysis, by means of information from simultaneously measured EMG signals of this moving person to decrease influence of muscle noises on the ECG signals.

8. Method for recognizing and measuring heartbeat during physical training, comprising:

recognizing and measuring individual heartbeats from ECG signals of a heart from an area of a waist and/or on an area of a body below the waist by means of electrodes integrated into an outfit or to a part of an outfit and/or by means of electrodes integrated to one or several wearable sensors, which electrodes are placed on different parts of the body, measuring two or more of the ECG signals received from the heart simultaneously from different directions from the heart, for recognizing individual heartbeats and measuring a time difference between actual heartbeats, by means of three or more said electrodes comprising receiving at least two of the ECG signals of one heartbeat, which are simultaneous but differ from each other, processing and analyzing the ECG signals at least two different ways to highlight moments of QRS peaks of the heartbeats for improving reliability of calculation and for decreasing the impact of disturbances, processing ECG signals, taken from a moving person for analysis, by means of information from the simultaneously measured motion signals of this moving person for decreasing influence of motion noises.

* * * * *

UNITED STATES PATENT AND TRADEMARK OFFICE
CERTIFICATE OF CORRECTION

PATENT NO. : 7,797,039 B2  Page 1 of 1
APPLICATION NO. : 11/393332
DATED : September 14, 2010
INVENTOR(S) : Koivumaa et al.

It is certified that error appears in the above-identified patent and that said Letters Patent is hereby corrected as shown below:

Claim 1, col. 8, line 25 insert --signals-- in between "ECG" and "at".

Claim 7, col. 9, line 10 delete "BCG" and insert -- ECG --.

Signed and Sealed this

Ninth Day of November, 2010

David J. Kappos
*Director of the United States Patent and Trademark Office*